US009285364B2

(12) United States Patent
Vordermeier et al.

(10) Patent No.: US 9,285,364 B2

(45) Date of Patent: Mar. 15, 2016

(54) MYCOBACTERIUM ANTIGENS

(71) Applicant: The Secretary of State for Environment, Food & Rural Affairs acting through the Animal Health and Veterinary Laboratories Agency, Worcester, Worcestershire (GB)

(72) Inventors: Hans Martin Vordermeier, Addlestone (GB); Benjamin Sidders, Great Shelford (GB); Neil Graham Stoker, London (GB); Katie Ewer, Oxford (GB)

(73) Assignee: The Secretary of State for Environment, Food and Rural Affairs, Addlestone, Surrey (GB)

( * ) Notice: Subject to any disclaimer, the term of this patent is extended or adjusted under 35 U.S.C. 154(b) by 0 days.

(21) Appl. No.: 14/186,291

(22) Filed: Feb. 21, 2014

(65) Prior Publication Data

US 2014/0296091 A1 Oct. 2, 2014

Related U.S. Application Data

(63) Continuation of application No. 12/742,223, filed as application No. PCT/GB2008/003724 on Nov. 6, 2008, now Pat. No. 8,697,091.

(30) Foreign Application Priority Data

Nov. 10, 2007 (GB) .................................. 0722105.4

(51) Int. Cl.

| | |
|---|---|
| ***A61K 39/04*** | (2006.01) |
| ***A61K 39/02*** | (2006.01) |
| ***A61K 39/00*** | (2006.01) |
| ***G01N 33/569*** | (2006.01) |
| ***C07K 14/35*** | (2006.01) |

(52) U.S. Cl.

CPC ............ *G01N 33/5695* (2013.01); *C07K 14/35* (2013.01); *A61K 39/00* (2013.01); *A61K 39/02* (2013.01); *A61K 39/04* (2013.01)

(58) Field of Classification Search

CPC ........ A61K 39/00; A61K 39/02; A61K 39/04

USPC .................. 424/9.1, 9.2, 184.1, 185.1, 234.1, 424/248.1; 530/300, 350; 536/23.1, 23.7

See application file for complete search history.

(56) References Cited

U.S. PATENT DOCUMENTS

2003/0129601 A1 7/2003 Cole
2004/0197896 A1* 10/2004 Cole .......................... 435/252.3
2012/0128708 A1 5/2012 Lalvani

FOREIGN PATENT DOCUMENTS

EP 1437367 A1 7/2004
WO PCT-WO 02/074903 A2 9/2002
WO PCT-WO 2008/028489 A2 3/2008
WO PCT-WO 2009/024822 A2 2/2009
WO PCT-WO 2010/115989 A1 10/2010

OTHER PUBLICATIONS

Bacon et al, Tuberculosis, (2004), pp. 205-217, vol. 84.
Baird et al, Nucleic Acids Research, (1988), p. 9047, vol. 144, No. 18.
Berthet et al, Microbiology, (1998), pp. 3195-3203, vol. 144.
Camus et al, "Re-annotation of the Genome Sequence of Mycobacterium Tuberculosis H37Rv," Microbiology, (2002), pp. 2967-2973, vol. 148.
Cockle et al, Infection and Ummunity, (2002), pp. 6996-7003, vol. 70, No. 12.
Colditz et al, Journal of the American medical Association, (1994), pp. 698-702, vol. 271, No. 9.
Coler et al, The Journal of Immunology, (1998), pp. 2356-2364, vol. 161.
Corbett et al, Archives of Internal Medicine, (2003), pp. 1009-1021, vol. 163.
Derfa, Breakdown of Bovine 1B Expenditure from England bTB programme (1998).
Ewer et al, Clinical and Vaccine Immunology, (Jan. 2006), pp. 90-97, vol. 13, No. 1.
Fine, The Lancet, (1995), pp. 1339-1345, vol. 346.
Fortune et al, Proceedings of the National Academy of Sciences, (2005), pp. 10676-1068, vol. 102, No. 30.
Garnier, et al, The Complete Genome Sequence of Mycobacterium Bovis, P.N.A.S., (2003), pp. 7877-7882, vol. 100, No. 13.
Harboe et al, Infection and Immunity, (1986), pp. 293-302, vol. 52, No. 1.
Harth et al, Infection and Immunity, (1996), pp. 3038-3047, vol. 64, No. 8.
Lawrence, Henderson's Dictionary of Biological Terms—"peptide", 11th Edition, John Wiley & Sons, 1995, p. 423.
MacGurn et al, Molecular Biology, (2005), pp. 1653-1663, vol. 57, No. 6.
Miller et al, Science, (1970), pp. 392-395, vol. 169.
Millington, et al., Rv3615c is a highly immunodominant RD1 (Region of Difference 1)-dependent secreted antigen specific for Mycobacterium tuberculosis infection, Proc Natl Acad Sci U S A., Apr. 5, 2011, published online Mar. 22, 2011, 108(14):5730-5735.
Mustafa et al, Infection and Immunity, (Aug. 2006), pp. 4566-4572, vol. 74, No. 8.
NCBI Accession No. NP_218132, Nov. 29, 2007.
NCBI Accession No. NP_857284, Jun. 3, 2010.
Rogerson et al, Immunology, (2005), pp. 195-201, vol. 118.
Shinnick et al, Journal of Bacteriology, (1987), pp. 1080-1088, vol. 169, No. 3.

(Continued)

*Primary Examiner* — Rodney P Swartz

(74) *Attorney, Agent, or Firm* — Howson & Howson LLP

(57) ABSTRACT

There is provided a diagnostic reagent for use in the detection of *M. bovis* or *M. tuberculosis* infection in an animal, comprising a peptide which has an epitope from *Mycobacterium bovis* hypothetic protein Mb3645c (SEQ ID NO: 1) or an epitope from a polypeptide having at least 76% identity with SEQ ID NO: 1.

22 Claims, 5 Drawing Sheets

(56) References Cited

OTHER PUBLICATIONS

Sidders B. et al, "Screening of Highly Expressed Mycobacterial Genes Identifies Rv3615c as a Useful Differential Diagnostic Antigen for the Mycobacterium Tuberculosis Complex," Infection and Immunity, (Sep. 2008), pp. 3932-3939, vol. 76, No. 9.
Skjot et al, Infection and Immunity, (2002), pp. 5446-5453, vol. 70, No. 10.
Sorensen et al, Infection and Immunity, (1995), pp. 1710-1717, vol. 63, No. 5.
Vordermeier et al, Infection and Immunity, (2002), pp. 3026-3032, vol. 70, No. 6.
Vordermeier et al, Infection and Immunity, (2003), pp. 1980-1987, vol. 71, No. 4.
Vordermeier et al., "Use of Synthetic Peptides Derived from the Antigens ESAT-6 and CFP-10 for Differential Diagnosis of Bovine Tuberculosis in Cattle," Clinical and Diagnostic Laboratory Immunology, (2001), pp. 571-578, vol. 8, No. 3, XP003009921.
Wood et al, Tuberculosis, (2001), pp. 147-155, vol. 81, Nos. 1/2.
United Kingdom Search Report for United Kingdom Patent Application No. GB0722105.4, Mar. 5, 2008.
International Search Report for International Patent Application No. PCT/GB2008/003724, Feb. 9, 2009.
Written Opinion for International Patent Application No. PCT/GB2008/003724, Feb. 9, 2009.
Buddle, et al., Identification of immune response correlates for protection against bovine tuberculosis, Veterinary Immunology and Immunopathology, Oct. 2005, pp. 45-51.
Raghavan, et al., Secreted transcription factor controls *Mycobacterium tuberculosis* virulence, Nature, Aug. 2008, vol. 454, pp. 717-721.
Arlehamn, et al., Memory T Cells in Latent *Mycobacterium tuberculosis* Infection Are Directed against Three Antigenic Islands and Largely Contained in a CXCR3+CCR6+ Th1 Subset, PLoS Pathogens, Jan. 2013, vol. 9, Issue 1, e1003130.
Brandt, et al., Key Epitopes on the ESAT-6 Antigen Recognized in Mice During the Recall of Protective Immunity to *Mycobacterium tuberculosis*, J. Immunol., Oct. 1996, pp. 3527-3533.
Cole, et al., Deciphering the biology of *Mycobacterium tuberculosis* from the complete genome sequence, *Nature*, Nov. 1998, pp. 537-544.
Ravn, et al., Human T Cell Responses to the ESAT-6 Antigen from *Mycobacterium tuberculosis*, J. Infect. Dis., Mar. 1999, pp. 637-645.
Jun. 18, 2014 Office Action in Canadian Patent Application No. 2,703,395 (claims common priority).
Dec. 12, 2014 Response to Jun. 18, 2014 Office Action in Canadian Patent Application No. 2,703,395.
Oct. 4, 2013 Communication in European Patent Application No. 13182794.1 (claims common priority).
May 14, 2014 Response to Oct. 4, 2013 Communication in European Patent Application No. 13182794.1.
Aug. 14, 2014 Communication in European Patent Application No. 13182794.1.
Oct. 6, 2014 Response to Aug. 14, 2014 Communication in European Patent Application No. 13182794.1.
Dec. 11, 2014 Communication in European Patent Application No. 13182794.1.
Apr. 8, 2015 Response to Dec. 11, 2014 Communication in European Patent Application No. 13182794.1.
Jun. 15, 2015 Communication in European Patent Application No. 13182794.1.
Jun. 25, 2015 Response to Jun. 15, 2015 Communication in European Patent Application No. 13182794.1.
Dec. 19, 2014 Communication in European Patent Application No. 14188545.9 (shares common priority).
Jun. 26, 2015 Response to Dec. 19, 2014 Communication in European Patent Application No. 14188545.9.

* cited by examiner

SEQUENCE LISTING

```
<160> NUMBER OF SEQ ID NOS: 25

<210> SEQ ID NO 1
<211> LENGTH: 103
<212> TYPE: PRT
<213> ORGANISM: Mycobacterium bovis

<400> SEQUENCE: 1

Met Thr Glu Asn Leu Thr Val Gln Pro Glu Arg Leu Gly Val Leu Ala
1               5                   10                  15

Ser His His Asp Asn Ala Ala Val Asp Ala Ser Ser Gly Val Glu Ala
            20                  25                  30

Ala Ala Gly Leu Gly Glu Ser Val Ala Ile Thr His Gly Pro Tyr Cys
        35                  40                  45

Ser Gln Phe Asn Asp Thr Leu Asn Val Tyr Leu Thr Ala His Asn Ala
    50                  55                  60

Leu Gly Ser Ser Leu His Thr Ala Gly Val Asp Leu Ala Lys Ser Leu
65                  70                  75                  80

Arg Ile Ala Ala Lys Ile Tyr Ser Glu Ala Asp Glu Ala Trp Arg Lys
                85                  90                  95

Ala Ile Asp Gly Leu Phe Thr
            100


<210> SEQ ID NO 2
<211> LENGTH: 20
<212> TYPE: PRT
<213> ORGANISM: Artificial
<220> FEATURE:
<223> OTHER INFORMATION: fragment of full length protein

<400> SEQUENCE: 2

Met Thr Glu Asn Leu Thr Val Gln Pro Glu Arg Leu Gly Val Leu Ala
1               5                   10                  15

Ser His His Asp
            20


<210> SEQ ID NO 3
<211> LENGTH: 20
<212> TYPE: PRT
<213> ORGANISM: Artificial
<220> FEATURE:
<223> OTHER INFORMATION: fragment of full length protein

<400> SEQUENCE: 3

Pro Glu Arg Leu Gly Val Leu Ala Ser His His Asp Asn Ala Ala Val
1               5                   10                  15

Asp Ala Ser Ser
            20


<210> SEQ ID NO 4
<211> LENGTH: 20
<212> TYPE: PRT
<213> ORGANISM: Artificial
<220> FEATURE:
<223> OTHER INFORMATION: fragment of full length protein
```

-continued

<400> SEQUENCE: 4

Ser His His Asp Asn Ala Ala Val Asp Ala Ser Ser Gly Val Glu Ala
1 5 10 15

Ala Ala Gly Leu
20

<210> SEQ ID NO 5
<211> LENGTH: 20
<212> TYPE: PRT
<213> ORGANISM: Artificial
<220> FEATURE:
<223> OTHER INFORMATION: fragment of full length protein

<400> SEQUENCE: 5

Asp Ala Ser Ser Gly Val Glu Ala Ala Ala Gly Leu Gly Glu Ser Val
1 5 10 15

Ala Ile Thr His
20

<210> SEQ ID NO 6
<211> LENGTH: 20
<212> TYPE: PRT
<213> ORGANISM: Artificial
<220> FEATURE:
<223> OTHER INFORMATION: fragment of full length protein

<400> SEQUENCE: 6

Ala Ala Gly Leu Gly Glu Ser Val Ala Ile Thr His Gly Pro Tyr Cys
1 5 10 15

Ser Gln Phe Asn
20

<210> SEQ ID NO 7
<211> LENGTH: 20
<212> TYPE: PRT
<213> ORGANISM: Artificial
<220> FEATURE:
<223> OTHER INFORMATION: fragment of full length protein

<400> SEQUENCE: 7

Ala Ile Thr His Gly Pro Tyr Cys Ser Gln Phe Asn Asp Thr Leu Asn
1 5 10 15

Val Tyr Leu Thr
20

<210> SEQ ID NO 8
<211> LENGTH: 20
<212> TYPE: PRT
<213> ORGANISM: Artificial
<220> FEATURE:
<223> OTHER INFORMATION: fragment of full length protein

<400> SEQUENCE: 8

Ser Gln Phe Asn Asp Thr Leu Asn Val Tyr Leu Thr Ala His Asn Ala
1 5 10 15

Leu Gly Ser Ser
20

<210> SEQ ID NO 9
<211> LENGTH: 20
<212> TYPE: PRT
<213> ORGANISM: Artificial
<220> FEATURE:
<223> OTHER INFORMATION: fragment of full length protein -continued

<400> SEQUENCE: 9

```
Val Tyr Leu Thr Ala His Asn Ala Leu Gly Ser Ser Leu His Thr Ala
1               5                   10                  15

Gly Val Asp Leu
            20
```

<210> SEQ ID NO 10
<211> LENGTH: 20
<212> TYPE: PRT
<213> ORGANISM: Artificial
<220> FEATURE:
<223> OTHER INFORMATION: fragment of full length protein

<400> SEQUENCE: 10

```
Leu Gly Ser Ser Leu His Thr Ala Gly Val Asp Leu Ala Lys Ser Leu
1               5                   10                  15

Arg Ile Ala Ala
            20
```

<210> SEQ ID NO 11
<211> LENGTH: 20
<212> TYPE: PRT
<213> ORGANISM: Artificial
<220> FEATURE:
<223> OTHER INFORMATION: fragment of full length protein

<400> SEQUENCE: 11

```
Gly Val Asp Leu Ala Lys Ser Leu Arg Ile Ala Ala Lys Ile Tyr Ser
1               5                   10                  15

Glu Ala Asp Glu
            20
```

<210> SEQ ID NO 12
<211> LENGTH: 20
<212> TYPE: PRT
<213> ORGANISM: Artificial
<220> FEATURE:
<223> OTHER INFORMATION: fragment of full length protein

<400> SEQUENCE: 12

```
Arg Ile Ala Ala Lys Ile Tyr Ser Glu Ala Asp Glu Ala Trp Arg Lys
1               5                   10                  15

Ala Ile Asp Gly
            20
```

<210> SEQ ID NO 13
<211> LENGTH: 20
<212> TYPE: PRT
<213> ORGANISM: Artificial
<220> FEATURE:
<223> OTHER INFORMATION: fragment of full length protein

<400> SEQUENCE: 13

```
Ala Lys Ile Tyr Ser Glu Ala Asp Glu Ala Trp Arg Lys Ala Ile Asp
1               5                   10                  15

Gly Leu Phe Thr
            20
```

<210> SEQ ID NO 14
<211> LENGTH: 95
<212> TYPE: PRT
<213> ORGANISM: Mycobacterium bovis -continued

<400> SEQUENCE: 14

Met Thr Glu Gln Gln Trp Asn Phe Ala Gly Ile Glu Ala Ala Ala Ser
1 5 10 15

Ala Ile Gln Gly Asn Val Thr Ser Ile His Ser Leu Leu Asp Glu Gly
20 25 30

Lys Gln Ser Leu Thr Lys Leu Ala Ala Ala Trp Gly Gly Ser Gly Ser
35 40 45

Glu Ala Tyr Gln Gly Val Gln Gln Lys Trp Asp Ala Thr Ala Thr Glu
50 55 60

Leu Asn Asn Ala Leu Gln Asn Leu Ala Arg Thr Ile Ser Glu Ala Gly
65 70 75 80

Gln Ala Met Ala Ser Thr Glu Gly Asn Val Thr Gly Met Phe Ala
85 90 95

<210> SEQ ID NO 15
<211> LENGTH: 100
<212> TYPE: PRT
<213> ORGANISM: Mycobacterium bovis

<400> SEQUENCE: 15

Met Ala Glu Met Lys Thr Asp Ala Ala Thr Leu Ala Gln Glu Ala Gly
1 5 10 15

Asn Phe Glu Arg Ile Ser Gly Asp Leu Lys Thr Gln Ile Asp Gln Val
20 25 30

Glu Ser Thr Ala Gly Ser Leu Gln Gly Gln Trp Arg Gly Ala Ala Gly
35 40 45

Thr Ala Ala Gln Ala Ala Val Val Arg Phe Gln Glu Ala Ala Asn Lys
50 55 60

Gln Lys Gln Glu Leu Asp Glu Ile Ser Thr Asn Ile Arg Gln Ala Gly
65 70 75 80

Val Gln Tyr Ser Arg Ala Asp Glu Glu Gln Gln Gln Ala Leu Ser Ser
85 90 95

Gln Met Gly Phe
100

<210> SEQ ID NO 16
<211> LENGTH: 16
<212> TYPE: PRT
<213> ORGANISM: Artificial
<220> FEATURE:
<223> OTHER INFORMATION: fragment of full length protein

<400> SEQUENCE: 16

Met Thr Glu Gln Gln Trp Asn Phe Ala Gly Ile Glu Ala Ala Ala Ser
1 5 10 15

<210> SEQ ID NO 17
<211> LENGTH: 16
<212> TYPE: PRT
<213> ORGANISM: Artificial
<220> FEATURE:
<223> OTHER INFORMATION: fragment of full length protein

<400> SEQUENCE: 17

Ala Gly Ile Glu Ala Ala Ala Ser Ala Ile Gln Gly Asn Val Thr Ser
1 5 10 15

<210> SEQ ID NO 18
<211> LENGTH: 16
<212> TYPE: PRT

<213> ORGANISM: Artificial
<220> FEATURE:
<223> OTHER INFORMATION: fragment of full length protein

<400> SEQUENCE: 18

Ala Ile Gln Gly Asn Val Thr Ser Ile His Ser Leu Leu Asp Glu Gly
1 5 10 15

<210> SEQ ID NO 19
<211> LENGTH: 16
<212> TYPE: PRT
<213> ORGANISM: Artificial
<220> FEATURE:
<223> OTHER INFORMATION: fragment of full length protein

<400> SEQUENCE: 19

Lys Trp Asp Ala Thr Ala Thr Glu Leu Asn Asn Ala Leu Gln Asn Leu
1 5 10 15

<210> SEQ ID NO 20
<211> LENGTH: 16
<212> TYPE: PRT
<213> ORGANISM: Artificial
<220> FEATURE:
<223> OTHER INFORMATION: fragment of full length protein

<400> SEQUENCE: 20

Gly Gln Ala Met Ala Ser Thr Glu Gly Asn Val Thr Gly Met Phe Ala
1 5 10 15

<210> SEQ ID NO 21
<211> LENGTH: 18
<212> TYPE: PRT
<213> ORGANISM: Artificial
<220> FEATURE:
<223> OTHER INFORMATION: fragment of full length protein

<400> SEQUENCE: 21

Met Ala Glu Met Lys Thr Asp Ala Ala Thr Leu Ala Gln Glu Ala Gly
1 5 10 15

Asn Phe

<210> SEQ ID NO 22
<211> LENGTH: 16
<212> TYPE: PRT
<213> ORGANISM: Artificial
<220> FEATURE:
<223> OTHER INFORMATION: fragment of full length protein

<400> SEQUENCE: 22

Gln Glu Ala Gly Asn Phe Glu Arg Ile Ser Gly Asp Leu Lys Thr Gln
1 5 10 15

<210> SEQ ID NO 23
<211> LENGTH: 18
<212> TYPE: PRT
<213> ORGANISM: Artificial
<220> FEATURE:
<223> OTHER INFORMATION: fragment of full length protein

<400> SEQUENCE: 23

Val Val Arg Phe Gln Glu Ala Ala Asn Lys Gln Lys Gln Glu Leu Asp
1 5 10 15

Glu Ile

-continued

```
<210> SEQ ID NO 24
<211> LENGTH: 18
<212> TYPE: PRT
<213> ORGANISM: Artificial
<220> FEATURE:
<223> OTHER INFORMATION: fragment of full length protein

<400> SEQUENCE: 24

Asn Ile Arg Gln Ala Gly Val Gln Tyr Ser Arg Ala Asp Glu Glu Gln
1               5                   10                  15

Gln Gln


<210> SEQ ID NO 25
<211> LENGTH: 16
<212> TYPE: PRT
<213> ORGANISM: Artificial
<220> FEATURE:
<223> OTHER INFORMATION: fragment of full length protein

<400> SEQUENCE: 25

Arg Ala Asp Glu Glu Gln Gln Gln Ala Leu Ser Ser Gln Met Gly Phe
1               5                   10                  15
```

MYCOBACTERIUM ANTIGENS

CROSS-REFERENCE TO RELATED APPLICATIONS

This application is a continuation of U.S. patent application Ser. No. 12/742,223, filed May 10, 2010 (all 35 U.S.C. 371 requirements completed on Aug. 25, 2010), which is a national stage of PCT/GB2008/003724, filed Nov. 6, 2008, which applications are incorporated herein by reference in their entireties.

FIELD OF INVENTION

The present invention relates to antigens for use in the detection of *mycobacterium* infections, particularly *Mycobacterium tuberculosis* and *M. bovis*, in mammals such as cattle.

BACKGROUND OF THE INVENTION

*M. tuberculosis* and *M. bovis* are important pathogens of man and animals. *M. tuberculosis* is thought to infect up to a third of the world's human population, remaining undetected during a latent phase of infection and reactivating to cause 10 million cases of *tuberculosis* and other diseases per year resulting in 2 million deaths (Corbett et al., 2003). *M. bovis*, which has more than 99.9% sequence identity with *M. tuberculosis*, is the causative agent of bovine *tuberculosis* (BTB) and also causes disease in human. BTB represents a significant economic burden to the agricultural industries of various countries including the United Kingdom (Krebs, 1997; DEFRA, 2006).

Current methods of control for these mycobacterial infections centre on the live attenuated vaccine *M. bovis bacillus* Calmette-Guerin (BCG) and diagnosis using an intradermal skin test with a purified protein derivative (PPD, tuberculin) harvested from mycobacterial cultures. The PPD skin test relies on a cellular immune response which is mounted in cattle with a mycobacterial infection. BTB control measures as applied for example in the United Kingdom and other European countries comprise a "test and slaughter" strategy where a positive result to a routine skin test with the single intradermal comparative tuberculin test (SICTT), leads to mandatory slaughter. In human populations the BCG vaccine has been used. However, BCG vaccination programs are hampered by widely differing rates of protection in different populations with efficacies that range from 0 to 80% (Colditz et al., 1994; Fine, 1995). In addition, vaccination sensitises individuals to tuberculin thereby interfering with diagnosis.

In addition to BTB skin tests, blood-based diagnostic assays that measure antigen-induced lymphokine production such as the interferon gamma (IFN-γ) are also under consideration. The cytokine IFN-γ appears to be critical in the development of immunity to *M. tuberculosis*. For example, both mice with a disrupted IFN-γ gene and humans with mutated IFN-γ receptor are highly susceptible to mycobacterial infections. However, specificity constraints are associated with the use of PPD in such assays. These arise due to the crude mixture of *M. bovis* proteins that PPD contains, many of which are cross-reactive with the BCG vaccine strain and environmental mycobacterial species such as *M. avium* and *M. intracellulare.*

Previous studies have demonstrated that diagnostic reagents which distinguish between vaccinated and infected cattle can be developed using specific, defined antigens that are present in virulent *M. bovis* but absent from the BCG.

Genetic analysis of BCG has revealed that several large genomic regions have been deleted during attenuation and subsequent prolonged propagation in culture. These regions have been characterised, and antigens from one of these regions, RD1, have been studied extensively in several species including humans and cattle. For example, it has been demonstrated that protein or peptide cocktails composed of two RD1 region antigens, ESAT-6 and CFP-10, can be used to distinguish between *M. bovis* infected and BCG-vaccinated cattle. The ESAT-6/CFP-10 assay is reported to have a sensitivity of at least 77.9% in cattle with confirmed *tuberculosis*, and a specificity of 100% in BCG-vaccinated and non-vaccinated cattle (Vordermeier et al. 2001).

However, the level of sensitivity achieved with these antigens has not reached that of tuberculin. It would, therefore, be desirable to provide other antigens in order to achieve this desired sensitivity. The present invention accordingly addresses the problem of providing further discriminatory diagnostic reagents for the detection of mycobacterial infections.

Camus et al. (Microbiology (2002) 148 2967-2973) and the associated NCBI Accession no. NP_218132 is a disclosure of the genome sequence of *M. tuberculosis* H37Rv, including the gene encoding Rv3615c. There is no suggestion of the use of the Rv3615c polypeptide or portions of it within a reagent for use in detection of *M. bovis* or *M. tuberculosis* infection in an animal.

Gamier et al. (Proc. Natl. Acad. Sci. U.S.A. (2003) 100 7877-7882 and the associated NCBI Accession no. NP_857284 is a disclosure of the genome sequence of *M. bovis*, including the gene encoding Mb3645c. There is no suggestion of the use of the Mb3645c polypeptide or portions of it within a reagent for use in detection of *M. bovis* or *M. tuberculosis* infection in an animal.

US2003/0129601 discloses a comparison of the genome sequences of *M. tuberculosis* and *M. leprae* and reports a total of 644 common protein sequences. It is proposed that these sequence may have a variety of uses including potential as drug targets, diagnostic antigens or subunit vaccine compositions. The inventors for the present application have found that one of the sequences has particular efficacy in the diagnosis of *M. bovis* or *M. tuberculosis* infection.

SUMMARY OF INVENTION

According to the present invention there is provided a diagnostic reagent, in particular for use in the detection of *M. bovis* or *M. tuberculosis* infection in an animal, comprising a peptide which has an epitope from *M. bovis* hypothetic protein Mb3645c (SEQ ID NO: 1) or an epitope from a polypeptide having at least 76% identity with SEQ ID NO: 1. The animal may be a mammal and preferably is a human being or a bovine species, for example a domestic cow. Alternatively, the mammal may be a badger. In a further alternative, the animal may be a fish or a bird species. The detection may take place by analysis of a sample obtained from the animal, such as a blood, saliva, faecal or tissue sample.

*M. bovis* hypothetical protein Mb3645c has the amino acid sequence:

```
                                        (SEQ ID NO: 1).
MTENLTVQPE RLGVLASHHD NAAVDASSGV EAAAGLGESV

AITHGPYCSQ FNDTLNVYLT AHNALGSSLH TAGVDLAKSL

RIAAKIYSEA DEAWRKAIDG LFT
```

Mb3645c is the *M. bovis* equivalent of *M. tuberculosis* Rv3615c, which has an identical amino acid sequence. References herein to Mb3645c are, therefore, to be taken as including a reference to Rv3615c, unless otherwise implied or specified.

"Detection of infection" as mentioned above indicates that an animal which is infected with *M. bovis* or *M. tuberculosis* can be detected and, for example, may be distinguished from an animal which has been vaccinated against infection by one or both of these bacteria, for example, by use of the BCG vaccine. The ability to distinguish between these states using a peptide having an epitope from Mb3645c is surprising, in view of the presence of the nucleic acid sequence encoding this protein in all of *M. bovis, M. tuberculosis* and the live attenuated vaccine BCG.

As described below, it has surprisingly been found that the known hypothetical protein Mb3645c comprises an epitope which can be used for diagnostic purposes, for example in the specific recognition of an *M. bovis*- or *M. tuberculosis*-infected mammal. This is because of the inventors' unexpected discovery that, as mentioned above, although the gene encoding Mb3645c is present in all of *M. bovis, M. tuberculosis* and the live attenuated vaccine BCG, exposure of an animal or a sample from an animal to an epitope from Mb3645c only causes a detectable immune response in an animal infected with *M. bovis* or *M. tuberculosis* (or in a sample from such a animal). Such a response is not detectable in an uninfected animal (or a sample from one), even when that animal has been administered the BCG vaccine.

Based on an NCBI protein BLAST search, the closest known protein to Mb3645c (other than Rv3615c) is a hypothetical protein MAP3219c from *M. avium* which shares 75% sequence identity with Mb3645c. The present invention excludes any epitope in MAP3219c which is not also found in Mb3645c.

As used herein, the term "epitope" refers to the amino acids (typically a group of around 5 or more amino acids) within a peptide sequence which are essential in the generation of an immune response and which can, therefore, be used in a diagnostic test. The immune response may be an antibody mediated immune response, but may also be a non-antibody mediated immune response, for example, an immune response which can be detected by means of a cell-mediated immunity (CMI) assay. Therefore, the epitope may be one which is recognisable by a T cell, for example by binding of a T cell receptor to the epitope.

The epitope may comprise consecutive amino acids, or the amino acids forming the epitope may be spaced apart from one another. In the latter case, the nature of the amino acids between the amino acids forming the epitope may not be crucial to the activity and may be varied, provided that the tertiary structure of the epitope is maintained, for example so that an immune response such as a cell-mediated immune response can occur in response to the presence of the epitope. Determination of the amino acids which form an epitope or part of an epitope can be undertaken using routine methods. For example, one of a series of small mutations such as point mutations may be made to a peptide and the mutated peptide assayed to determine whether the immunogenic or diagnostic activity has been retained. Where it has, then the variant retains the epitope. If activity has been lost, then the mutation has disrupted the epitope and so must be reversed.

Suitably, the diagnostic peptide has less than 103 amino acids, for example up to 100 amino acids, for example up to 75 amino acids, for example up to 50 amino acids, for example up to 25 amino acids, for example up to 20 amino acids. It may comprise a truncated form of Mb3645c.

The diagnostic reagent peptide may comprise a series of consecutive amino acids from within SEQ ID NO: 1 or from within a polypeptide having at least 76% identity with SEQ ID NO: 1.

The diagnostic reagent peptide may comprise an epitope from (i.e., contained in) one or more of the group of peptides consisting of SEQ ID NOs 2-13, which are defined as follows:

```
                     (SEQ ID NO: 2);
MTENLTVQPE RLGVLASHHD

                     (SEQ ID NO: 3);
PERLGVLASH HDNAAVDASS

                     (SEQ ID NO: 4);
SHHDNAAVDA SSGVEAAAGL

                     (SEQ ID NO: 5);
DASSGVEAAA GLGESVAITH

                     (SEQ ID NO: 6);
AAGLGESVAI THGPYCSQFN

                     (SEQ ID NO: 7);
AITHGPYCSQ FNDTLNVYLT

                     (SEQ ID NO: 8);
SQFNDTLNVY LTAHNALGSS

                     (SEQ ID NO: 9);
VYLTAHNALG SSLHTAGVDL

                    (SEQ ID NO: 10);
LGSSLHTAGV DLAKSLRIAA

                    (SEQ ID NO: 11);
GVDLAKSLRI AAKIYSEADE

                (SEQ ID NO: 12); and
RIAAKIYSEA DEAWRKAIDG

                    (SEQ ID NO: 13).
AKIYSEADEA WRKAIDGLFT
```

The peptides of SEQ ID NO: 2-13 are overlapping 20-mer peptides which encompass the complete Mb3645c sequence of SEQ ID NO: 1. As demonstrated below, these peptides comprise epitopes which can be used for diagnostic purposes, for example in the specific recognition of an *M. bovis*- or *M. tuberculosis*-infected mammal.

In one embodiment of the invention, the diagnostic reagent comprises one or more peptides each selected from the group of peptides consisting of SEQ ID NOs: 1-13. The diagnostic reagent may comprise at least two, three, four, five, six, seven, eight, nine, ten or more peptides with an epitope from one or more peptides each selected from the group of peptides consisting of SEQ ID NOs: 1-13. For example, the diagnostic reagent may comprise at least two, three, four, five, six, seven, eight, nine, ten or more peptides each defined by any of SEQ ID NOs: 1-13.

In another embodiment, the diagnostic reagent comprises a peptide having an epitope from the peptide of SEQ ID NO: 12 and/or 13. This diagnostic reagent may for example comprise the peptide of SEQ ID NO: 12 and/or 13.

In a further embodiment, the diagnostic reagent comprises a peptide having one or more epitopes from one or more of the group of peptides consisting of SEQ ID NOs: 7, 8, 9, 10, 11, 12 and 13, or the group consisting of SEQ ID NOs: 9, 10, 11, 12 and 13 or the group consisting of SEQ ID NOs: 7, 8, 9, 10, 12 and 13. This diagnostic reagent may for example comprise any one or more peptides each selected from the group of peptides consisting of SEQ ID NOs: 9, 10, 11, 12 and 13. In another embodiment, the diagnostic reagent comprises a peptide having one or more epitopes from one or more of the group of peptides consisting of SEQ ID NOs: 2 and 9-13.

The peptides of SEQ ID NOs: 1 and 8, 9, 10, 11, 12 and 13 (especially 10, 11, 12 and 13) contain dominant epitopes recognised by bovine T cells and are therefore particularly useful in the diagnostic reagent of the invention.

The diagnostic reagent may, for example, comprise a combination of epitopes derived from any one or more of the groups of peptides set out below:

| SEQ ID NOs | SEQ ID NOs | SEQ ID NOs | SEQ ID NOs | SEQ ID NOs |
|---|---|---|---|---|
| 2, 9 | 2, 10 | 2, 11 | 2, 12 | 2, 13 |
| 2, 9, 10 | 2, 9, 11 | 2, 9, 12 | 2, 9, 13 | 2, 10, 11 |
| 2, 10, 12 | 2, 10, 13 | 2, 11, 12 | 2, 11, 13 | 2, 12, 13 |
| 2, 9, 10, 11 | 2, 9, 10, 12 | 2, 9, 10, 13 | 2, 10, 11, 12 | 2, 10, 11, 13 |
| 2, 11, 12, 13 | 2, 9, 10, 11, 12 | 2, 9, 10, 11, 13 | 2, 9, 10, 12, 13 | 9, 10 |
| 9, 11 | 9, 12 | 9, 13 | 9, 10, 11 | 9, 10, 12 |
| 9, 10, 13 | 9, 10, 11, 12 | 9, 10, 11, 13 | 9, 10, 12, 13 | 10, 11 |
| 10, 12 | 10, 13 | 10, 11, 12 | 10, 11, 13 | 10, 12, 13 |
| 11, 12 | 11, 13 | 11, 12, 13 | 12, 13 | 10, 12, 13 |
| 8, 9 | 8, 10 | 8, 12 | 8, 13 | 8, 9, 10 |
| 8, 10, 12 | 8, 12, 13 | 8, 9, 12 | 8, 9, 13 | 8, 10, 12 |
| 8, 10, 13 | 7, 8, 10, 12 | 8, 10, 12, 13 | 9, 10 | 9, 12 |
| 9, 13 | 9, 10, 12 | 9, 12, 13 | | |

The diagnostic reagent may thus comprise any combination of peptides selected from those listed above, or any combination of the listed combinations.

Alternatively, the diagnostic reagent may comprise peptides having all of the epitopes from the group of peptides consisting of, for example, SEQ ID NOs: 12-13, or consisting of SEQ ID NOs: 11-13, or consisting of SEQ ID NOs: 10-13, or consisting of SEQ ID NOs: 9-13, or consisting of SEQ ID NOs: 8-13, or consisting of SEQ ID NOs: 7-13, or consisting of SEQ ID NOs: 2-13. For example, the diagnostic reagent may comprise all of the peptides from the group of peptides consisting of, for example, SEQ ID NOs: 12-13, or consisting of SEQ ID NOs: 11-13, or consisting of SEQ ID NOs: 10-13, or consisting of SEQ ID NOs: 9-13, or consisting of SEQ ID NOs: 8-13, or consisting of SEQ ID NOs: 7-13, or consisting of SEQ ID NOs: 2-13.

The diagnostic reagent may also comprise a fusion peptide in which fragments derived from SEQ ID NO: 1 or a polypeptide having at least 76% identity thereto have been joined.

The diagnostic reagent Mb3645c-based peptides as defined herein may be used on their own or with one or more other peptides, for example to achieve greater sensitivity and/or specificity of a diagnostic test. For example, the diagnostic reagent may in addition comprise one or more polypeptides or peptides derived from ESAT-6 (SEQ ID NO: 14) and/or the CFP-10 (SEQ ID NO: 15) polypeptides, in which ESAT-6 has the amino acid sequence:

```
                                    (SEQ ID NO: 14);
MTEQQWNFAG IEAAASAIQG NVTSIHSLLD EGKQSLTKLA

AAWGGSGSEA YQGVQQKWDA TATELNNALQ NLARTISEAG

QAMASTEGNV TGMFA
```

and in which CFP-10 has the amino acid sequence:

```
                                    (SEQ ID NO: 15).
MAEMKTDAAT LAQEAGNFER ISGDLKTQID QVESTAGSLQ

GQWRGAAGTA AQAAVVRFQE AANKQKQELD EISTNIRQAG

VQYSRADEEQ QQALSSQMGF
```

For example, the peptides derived from ESAT-6 may be the peptides of SEQ ID NO: 16-21, which are:

```
                  (SEQ ID NO: 16);
MTEQQWNFAG IEAAAS

                  (SEQ ID NO: 17);
AGIEAAASAI QGNVTS

                  (SEQ ID NO: 18);
AIQGNVTSIH SLLDEG

              (SEQ ID NO: 19); and
KWDATATELN NALQNL

                  (SEQ ID NO: 20).
GQAMASTEGN VTGMFA
```

The peptides derived from CFP-10 may be the peptides of SEQ ID NOs 21-25, which are:

```
                  (SEQ ID NO: 21);
MAEMKTDAAT LAQEAGNF

                  (SEQ ID NO: 22);
QEAGNFERIS GDLKTQ

                  (SEQ ID NO: 23);
VVRFQEAANK QKQELDEI

              (SEQ ID NO: 24); and
NIRQAGVQYS RADEEQQQ

                  (SEQ ID NO: 25).
RADEEQQQAL SSQMGF
```

The ESAT-6 and CFP-10 peptides of SEQ ID NOs 16-25 have been disclosed in Vordemeier et al. (2001) and provide a useful diagnostic for detection of *M. bovis*- and/or *M. tuberculosis*-infected animals. Used in combination with the Mb3645c-derived peptides, as defined here, a more sensitive diagnostic reagent is obtained.

The diagnostic reagent according to present invention may accordingly be specific for *M. bovis* and/or *M. tuberculosis*.

The diagnostic reagent may be used in the detection of an *M. bovis*- and/or *M. tuberculosis*-infected mammal, for example an *M. bovis*-infected cow.

Also provided according to the present invention is a diagnostic kit comprising a diagnostic reagent as defined herein. The diagnostic reagent may, in particular, be able to detect an *M. bovis*- or *M. tuberculosis*-infected mammal Preferably, the diagnostic reagent is able to differentiate between an *M. bovis*- and/or *M. tuberculosis*-infected mammal and a mammal vaccinated against *M. bovis* or *M. tuberculosis* (for example, a mammal vaccinated with the live attenuated vaccine BCG).

The diagnostic kit may be of particular use in the detection of a *M. bovis*- and/or *M. tuberculosis*-infected mammal which is not susceptible to diagnosis by the ESAT-6/CFP-10 assay as described in Vordemeier et al. (2001).

The diagnostic kit may comprise one or more peptides each selected from those having amino acid sequences of SEQ ID NOs 1-13 and optionally additionally comprise one or more peptides each selected from those having amino acid sequences of SEQ ID NOs 16-25.

The diagnostic kit may be suitable for use in a cell-mediated immunity (CMI) assay. For example, the CMI assay may use detection of interferon gamma (IFN-γ) as a readout system in either EIA (Wood & Jones, 2001) or ELISPOT format (Vordermeier et al., 2002). As is well known to the skilled person, such assays do not depend on the detection of an antibody response but, instead, rely on recognition of an epitope by a T cell, for example via binding of a T cell receptor.

In a further aspect of the present invention there is provided an isolated peptide of between 5 to 100 amino acids in length, for example 8 to 100, 8 to 35, 8 to 25, 10 to 25 or 12-20 amino acids in length, in which the peptide has an epitope from *M. bovis* hypothetic protein Mb3645c (SEQ ID NO: 1) or from a polypeptide having at least 76% identity with SEQ ID NO: 1, and wherein the peptide has *M. bovis*- and/or *M. tuberculosis*-specific antigenic and/or immunogenic properties. The isolated peptide may be 5, 6, 7, 8, 9, 10, 11, 12, 13, 14, 15, 16, 17, 18, 19, 20, 21, 22, 23, 24 or 25 amino acids in length, for example 12 or 20 amino acids in length.

The term "*M. bovis*- and/or *M. tuberculosis*-specific antigenic and immunogenic properties" indicates that the peptide according to this aspect of the invention is detectable by means of an immunogenic assay, preferably by means of a cell-mediated immunity (CMI) assay.

The isolated peptide may have an amino acid sequence of any of SEQ ID NOs: 2-13, or may comprise a contiguous combination of one or more of these sequences (for example, any two of SEQ ID NOs: 2-13 joined together end-to-end).

The isolated peptide may be a peptide in which, compared with the corresponding section of SEQ ID NO: 1, various amino acids have been deleted. The peptide may thus be restricted to comprise the minimum number of amino acids required to maintain specificity against *M. bovis* and/or *M. tuberculosis*. For example, amino acid deletions may be acceptable provided that the tertirary structure of an epitope from SEQ ID NO:1 is maintained. A peptide modified in this way may be comprised within a fusion peptide.

The present invention also encompasses variants of the diagnostic reagent peptide and the isolated peptide. As used herein, a "variant" means a peptide in which the amino acid sequence differs from the base sequence from which it is derived in that one or more amino acids within the sequence are substituted for other amino acids. The variant is a functional variant, in that the functional characteristics of the peptide from which the variant is derived are maintained. For example, a similar immune response is elicited by exposure of an animal, or a sample from an animal, to the variant polypeptide. In particular, any amino acid substitutions, additions or deletions must not alter or significantly alter the tertiary structure of one or more epitopes contained within the peptide from which the variant is derived. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

As mentioned above, non-conservative substitutions are possible provided that these do not disrupt the tertiary structure of an epitope within the peptide, for example, which do not interrupt the immunogenicity (for example, the antigenicity) of the peptide.

Broadly speaking, fewer non-conservative substitutions will be possible without altering the biological activity of the polypeptide. Suitably, variants may be at least 50% identical, 60% identical, for example at least 75% identical, such as at least 90% identical to the base sequence.

Also provided is an isolated nucleic acid which encodes a diagnostic reagent peptide, an isolated peptide, or variants thereof, as defined herein, but excluding the known ESAT-6 and CFP-10 polypeptides and peptides defined by SEQ ID NO. 14-25. Using the standard genetic code, a nucleic acid encoding an epitope or peptide may readily be conceived and manufactured by the skilled person. The nucleic acid may be DNA or RNA, and where it is a DNA molecule, it may comprise a cDNA or genomic DNA. The invention encompasses fragments and variants of the isolated nucleic acid, where each such fragment or variant encodes a peptide with antigenic properties as defined herein. Fragments may suitably comprise at least 15, for example at least 30, or at least 60 consecutive bases from the basic sequence.

The term "variant" in relation to a nucleic acid sequences means any substitution of, variation of, modification of, replacement of deletion of, or addition of one or more nucleic acid(s) from or to a polynucleotide sequence providing the resultant peptide sequence encoded by the polynucleotide exhibits at least the same properties as the peptide encoded by the basic sequence. In this context, the properties to be conserved are the ability to form one or more epitopes such that an immune response is generated which is equivalent to that of the diagnostic reagent peptide or isolated peptide as defined herein. The term, therefore, includes allelic variants and also includes a polynucleotide which substantially hybridises to the polynucleotide sequence of the present invention. Such hybridisation may occur at or between low and high stringency conditions. In general terms, low stringency conditions can be defined a hybridisation in which the washing step takes place in a 0.330-0.825M NaCl buffer solution at a temperature of about 40-48° C. below the calculated or actual melting temperature ($T_m$) of the probe sequence (for example, about ambient laboratory temperature to about 55° C.), while high stringency conditions involve a wash in a 0.0165-0.0330M NaCl buffer solution at a temperature of about 5-10° C. below the calculated or actual $T_m$ of the probe (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (1989; Molecular Cloning, Cold Spring Harbor Laboratory Press, Cold Spring Harbor).

Typically, variants have 60% or more of the nucleotides in common with the nucleic acid sequence of the present invention, more typically 65%, 70%, 80%, 85%, or even 90%, 95%, 98% or 99% or greater sequence identity.

Peptides and nucleic acids of the invention may be isolated from strains of *M. bovis* and *M. tuberculosis*. However, they may be prepared synthetically using conventional peptide synthesisers. Alternatively, they may be produced using recombinant DNA technology or isolated from natural sources followed by any chemical modification, if required. In these cases, a nucleic acid encoding the peptide is incorporated into suitable expression vector, which is then used to transform a suitable host cell, such as a prokaryotic cell such as *E. coli*. The transformed host cells are cultured and the peptide isolated therefrom. Vectors, cells and methods of this type form further aspects of the present invention.

In another aspect of the invention, there is provided a method for diagnosing in a host an infection of, or exposure to, a *mycobacterium*, comprising the steps of:

i) contacting a population of cells from the host with a diagnostic reagent as defined herein; and
ii) determining whether the cells of said cell population recognise the diagnostic reagent.

The diagnostic reagent based on Mb3645c may be contacted together or separately from the diagnostic reagent based on ESAT-6/CFP-10.

The population of cells may include T-cells. Recognition of the diagnostic reagent by said cells may be by way of, for example, binding of a T cell receptor to the diagnostic reagent, for example, binding of the receptor to an epitope included within the diagnostic reagent. The *mycobacterium* may by *M. bovis* or *M. tuberculosis.*

The method for diagnosing may comprise a cell-mediated immunity (CMI) assay, for example a CMI assay which detects IFN-γ as described herein.

The term "polypeptide" as used herein includes long chain peptides, such as proteins and epitopic fragments thereof. The term "peptide" refers to smaller proteins, for example up to 100 amino acids in length.

Sequence identity between nucleotide and amino acid sequences can be determined by comparing an alignment of the sequences. When an equivalent position in the compared sequences is occupied by the same amino acid or base, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

Suitable computer programs for carrying out sequence comparisons are widely available in the commercial and public sector. Examples include the Gap program (Needleman & Wunsch, 1970, J. Mol. Biol. 48: 443-453) and the FASTA program (Altschul et al., 1990, J. Mol. Biol. 215: 403-410). Gap and FASTA are available as part of the Accelrys GCG Package Version 11.1 (Accelrys, Cambridge, UK), formerly known as the GCG Wisconsin Package. The FASTA program can alternatively be accessed publically from the European Bioinformatics Institute and the University of Virginia. FASTA may be used to search a sequence database with a given sequence or to compare two given sequences. Typically, default parameters set by the computer programs should be used when comparing sequences. The default parameters may change depending on the type and length of sequences being compared. A sequence comparison using the FASTA program may use default parameters of Ktup=2, Scoring matrix=Blosum50, gap=−10 and ext=−2.

BRIEF DESCRIPTION OF FIGURES

Particular non-limiting examples of the present invention will now be described with reference to the following Figures, in which.

EXAMPLES

Introduction

Figure 1:
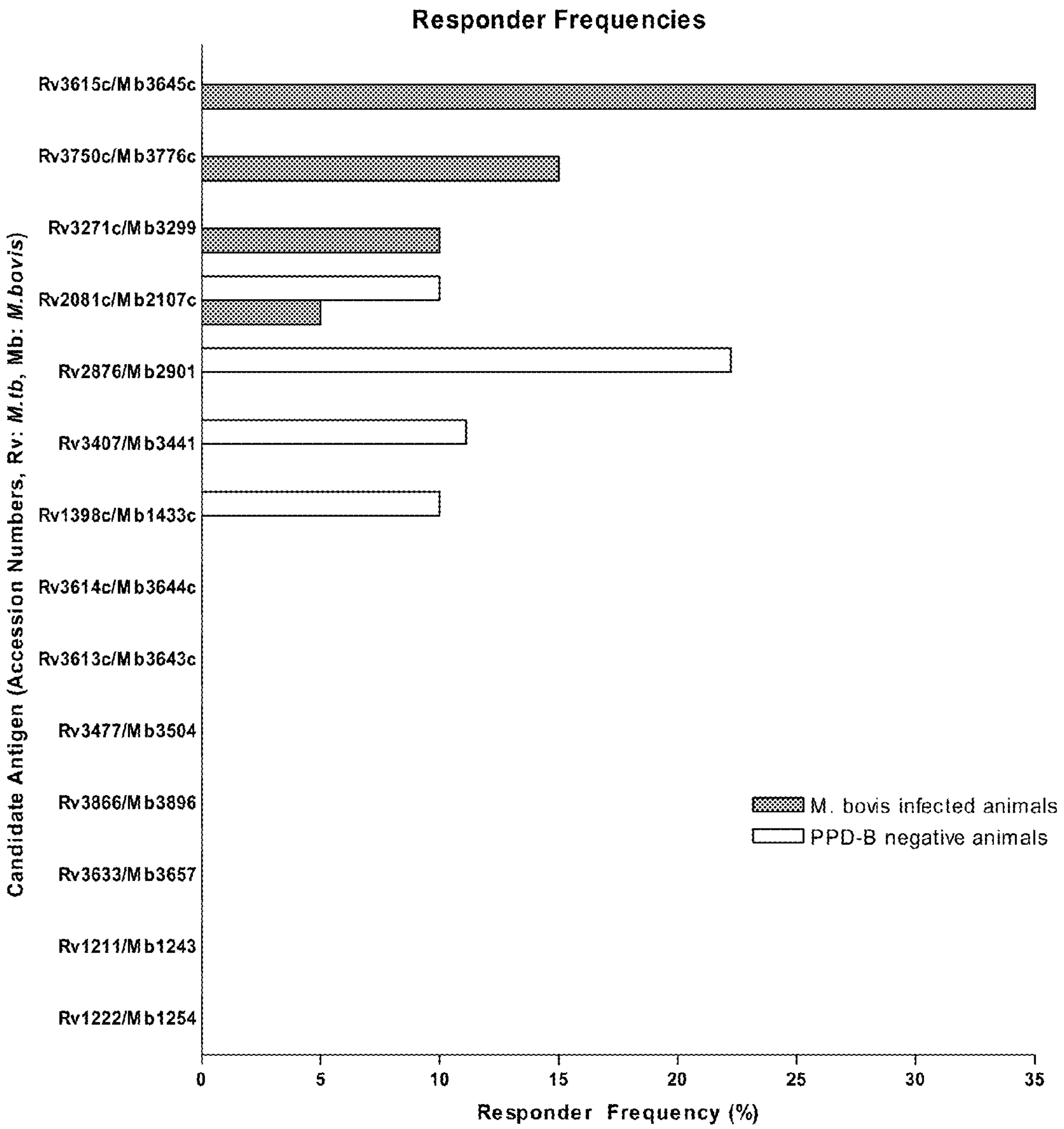
FIG. 1 is a histogram showing responder frequencies of screened candidate antigens.

The identification of new subunit vaccine candidates or diagnostic markers has been greatly enhanced with the development of various post-genomic approaches (Cockle et al., 2002; Ewer et al., 2006). These have largely involved sequence based analyses of the pathogen's genome. Here, the inventors took an alternative approach and focused on the transcriptional activity of genes to identify potential antigens. A method of microarray analysis was developed that quantifies gene expression on a global scale. As seen in Table 1, it was found that that many of the major mycobacterial antigens such as ESAT-6, CFP-10, Ag85B etc. are consistently highly expressed. Further to this, it was recently shown that the number of CD4+ T cells responsive to known mycobacterial antigens is closely related to the level of transcription of its gene (Rogerson et al., 2006).

With this as the basis, the inventors used a quantitative microarray analysis to identify genes that are consistently highly expressed in both *M. tuberculosis* and *M. bovis* across a variety of growth conditions. Fourteen of these genes were then selected and screened for their potential as immunogens and diagnostic markers of infection using *M. bovis* infected cattle. No evidence was found to support a link between mRNA abundance and antigenicity. However, surprisingly, the inventors still identified one antigen that discriminated between infected and vaccinated cattle. Further, the same antigen showed a marked response in infected cattle that do not respond to the classic mycobacterial antigens ESAT-6 and CFP-10, which will allow the antigen to increase the sensitivity of previously described differential diagnostic tests based upon ESAT-6 and CFP-10 (Vordemeier et al. 2001).

Methods

Selection of Candidate Antigens

Six microarray datasets were used in this study. All RNA extraction and microarray hybridisations were performed as detailed in Bacon et al. (2004). The Perl computing language and the R statistical environment were used to perform all further data and statistical analysis.

For each data set, genome-wide mRNA abundances were calculated as follows. Initially, all control spots on the array were removed from the dataset, including all representing ribosomal RNA. The local background noise, as determined by the image quantitation software, was subtracted from each spot. No data values were excluded from this study as it was reasoned that weak signals (after background subtraction) were reflective of low abundance transcripts.

For each spot i on the array the fluorescent intensity from the RNA channel was normalised by simple division to the fluorescent intensity of the gDNA channel:

$$\text{Normalised Intensity } (R_i)=\text{RNA}_i/\text{DNA}_i.$$

The correlation between hybridisation replicates within each dataset was confirmed to ensure there were no extreme outliers. Technical and biological replicates were then averaged to provide a single normalised intensity value for each gene on the array.

To account for an observed probe length bias, signal intensity was normalised to probe length using a model of linear regression of log intensity on probe length:

$$\text{Probe normalised intensity } (\log^e Rn_i)=\log^e R_i-(\text{intercept}+\text{slope}*\text{Probe Length}_i)$$

The corrected $\text{Rn}_i$ values were converted back to a raw scale and for ease of understanding are depicted as a proportional value, expressed in parts per million (ppm), based on the assumption that the sum of all intensity values represents the sum of the transcript (mRNA) population within the sample:

$$\text{ppm}=(Rn_i/\Sigma_{i\text{-}ith}Rn)*10^6$$

Candidate antigens were then selected based on their consistent high expression across all six of the datasets which come from a variety of experimental conditions: *M. tuberculosis* in aerobic and low oxygen chemostats, *M. tuberculosis* in batch culture, *M. tuberculosis* in macrophages, *M. bovis* in aerobic chemostats, and *M. bovis* in batch culture. Using these datasets, genes were selected which were consistently amongst the top 15% of abundant mRNA transcripts across all conditions in either *M. tuberculosis, M. bovis* or both. Candidates were further selected based on close amino acid homology between *M. tuberculosis* and *M. bovis* and little significant homology to other closely related species. Further to this, all candidates which had been tested previously were excluded. A total of 14 candidates were screened using 20mer overlapping peptides in this study (Table 1).

Cattle 10 uninfected control animals were obtained from herds within 4 yearly testing parishes with no history of a BTB breakdown in the past 4 years and tested for the absence of an in vitro IFNγ response to PPD-A and PPD-B, to confirm an absence of infection. A further 20 animals from similar BTB-free herds were vaccinated at least 6 months prior to sampling with $10^6$ CFU of BCG Danish strain 1331 (Statens Serum Institute, Copenhagen, Denmark) according to the manufacturer's instructions (reconstituted in Sautons medium and 1 ml injected subcutaneously).

Blood samples were obtained from 30 naturally infected, tuberculin skin test positive reactors within herds known to have BTB. All animals were additionally screened for an in vitro IFNγ response to PPD-B and the presence or absence of a response to ESAT-6 and CFP-10 was recorded. These animals were housed at VLA at the time of blood sampling. Infection was confirmed by necroscopy and/or *M. bovis* culture.

Production of Peptides

Bovine tuberculin (PPD-B) and avian tuberculin (PPD-A) were supplied by the Tuberculin Production Unit at the Veterinary Laboratories Agency, Weybridge, Surrey UK and were used to stimulate whole blood at 10 $\mu g \cdot ml^{-1}$. Staphylococcal enterotoxin B was included as a positive control at 5 $\mu g \cdot ml^{-1}$.

Peptides representing our candidates were pin synthesised as 20-mers spanning the length of all 14 proteins with each peptide overlapping its neighbour by 12 amino acid residues (Pepscan, Lelystad, Netherlands). These were dissolved in Hanks Balanced Salt Solution (Gibco) and 20% DMSO to 5 $\mu g\ ml^{-1}$ and grouped by gene into 26 pools of 8 to 12 peptides, with some genes represented by more than one pool. Pools were used to stimulate whole-blood at a final concentration of 10 $\mu g \cdot ml^{-1}$ total peptide. Peptides from the ESAT-6 and CFP-10 proteins were synthesised, quality assessed and formulated into a peptide cocktail as previously described (Vordermeier et al., 2001).

IFN-γ Enzyme-Linked Immunosorbent Assay

Whole-blood cultures were performed in 96-well plates where 250 μl whole blood aliquots were mixed with antigen-containing solution to a final concentration of 10 $\mu g \cdot ml^{-1}$. Serum containing supernatants were harvested after 24 hours of culture at 37° C. and 5% $CO_2$ in a humidified incubator. The IFNγ concentration was determined using the BOVIGAM ELISA kit (Prionics AG, Switzerland). Results were deemed positive when the optical densities at 450 nm ($OD_{450}$) with antigens minus the $OD_{450}$ without antigens were ≥0.1. For comparative analysis of PPD-B versus PPD-A responses, a positive result was defined as a PPD-B $OD_{450}$ minus PPD-A $OD_{450}$ of ≥0.1 and a PPD-B $OD_{450}$ minus unstimulated $OD_{450}$ of ≥0.1.

BOVIGAM Data Analysis

All raw data from the BOVIGAM screening was handled using a PERL program, boviAnalyser.pl, which evoked analytical routines in the statistical environment R (R-Development-Core-Team, 2006). Graphs were generated using both R and Graph-Pad Prism v4.

Ex Vivo IFN-γ Enzyme-Linked Immunospot (ELISPOT) Assay

Peripheral blood mononuclear cells (PBMC) were isolated from heparinized blood taken from three cattle which had previously exhibited an in vitro response to the Rv3615c peptide pool. Separation was performed using Histopaque 1077 (Sigma) gradient centrifugation, and the cells were resuspended in RPMI 1640 tissue culture medium containing 25 mM HEPES (Gibco), 10% fetal calf serum, 1% nonessential amino acids, $5\times10^{-5}$ M β-mercaptoethanol, 100 U/ml penicillin, and 100 $\mu g\ ml^{-1}$ streptomycin. Cells were enumerated, and suspensions containing $2\times10^6$ cells $ml^{-1}$ were prepared. IFN-γ production by PBMC was analyzed using a Mabtech bovine IFN-γ ELISPOT kit (Mabtech, Stockholm, Sweden). The ELISPOT plates (Multiscreen HTS-IP; Millipore) were coated at 4° C. overnight with a bovine IFN-γ-specific monoclonal antibody, after which the wells were blocked for 2 h using 10% fetal calf serum in RPMI 1640. The primary antibody and blocking buffer were removed from the plates, and PBMC suspended in tissue culture medium were then added ($2\times10^5$ cells $well^{-1}$) and incubated overnight at 37° C. with 5% CO2 in the presence of the individual antigens. Stimulation was performed using the peptides at a concentration of 5 μg $ml^{-1}$ or a pool of all 12 peptides containing 5 μg $ml^{-1}$ of each peptide. The wells were washed using phosphatebuffered saline plus 0.05% Tween 80. A secondary biotinylated antibody was used at a concentration of 0.025 μg $ml^{-1}$ and this was followed by incubation with streptavidin-linked horseradish peroxidase. After a further wash, the spot-forming cells were visualized using an AEC chromogen kit (Sigma). Spots were counted using an AID ELISPOT reader and EliSpot 4.0 software (Autoimmun Diagnostika, Germany).

Fluorescence-Assisted Cell Sorting (FACS) Analysis

PBMC were isolated from fresh heparinized blood as described above for the ELISPOT assay and enumerated. Then a suspension containing $2\times10^6$ cells $ml^{-1}$ was prepared and incubated overnight in a 24-well plate (Nunc) at 37° C. in the presence of 5% CO2 with either RPMI medium (unstimulated control), PPD-B, pokeweed mitogen (positive control), individual peptides at a concentration of 5 μg $ml^{-1}$, or a pool of all 12 peptides at a concentration of 5 μg $ml^{-1}$. After incubation, brefeldin A (Sigma) was added at a concentration of 10 μg $ml^{-1}$, and the preparation was incubated for a further 4 h. The plate was centrifuged at 300×g for 5 min, and the cells were resuspended in 250 μl (final volume) for transfer to a 96-well plate. Surface antibody staining was performed using Alexa Fluor 647-conjugated anti-CD4 (code MCA1653A627; Serotec) and fluorescein isothiocyanate-conjugated anti-CD8 (code MCA837F; Serotec) antibodies. Differential "live/dead" staining was performed using Vivid (Invitrogen). After incubation for 15 min at 4° C., cells were washed and centrifuged before they were permeabilized using Cytofix/Cytoperm (BD) at 4° C. for 20 min and stored overnight at 4° C. Intracellular staining for IFN-γ was performed using R-phycoerythrin-conjugated anti-IFN-γ (Serotec) for 30 min at 4° C. Cells were finally suspended in 600 of buffer and analyzed using a Cyan ADP instrument and the Summit 4.3 software (Dako, Denmark).

Results

Genes that had been found to be consistently highly expressed in *M. tuberculosis* and *M. bovis* across a variety of growth conditions (termed members of the abundant invariome) were assessed for the presence of known antigens. Ten previously well characterised antigens were found to be a part of this abundant invariome (Table 1), which suggested that other consistently highly expressed genes could also be antigenic.

TABLE 1

Mycobacterial antigens found to be highly expressed across a variety of growth conditions

| Rv | Name | Avg PPM | StDev | Reference |
|---|---|---|---|---|
| Rv0288 | cfp7 | 781 | 286 | (Skjot et al., 2002) |
| Rv0440 | groEL2 | 4438 | 2385 | (Shinnick, 1987) |
| Rv1174c | Mpt8.4 | 1165 | 424 | (Coler et al., 1998) |
| Rv1886c | fbpB/Ag85B | 1464 | 1168 | (Harth et al., 1996) |
| Rv1987 | Rv1987 | 495 | 136 | (Cockle et al., 2002) |
| Rv1980c | mpt64 | 1316 | 629 | (Harboe et al., 1986) |
| Rv3418c | groES | 5189 | 2593 | (Baird et al., 1988) |
| Rv3616c | Rv3616c | 2619 | 1457 | (Mustafa et al., 2006) |
| Rv3874 | cfp10 | 5414 | 3950 | (Sorensen et al., 1995) |
| Rv3875 | esat6 | 2472 | 1229 | (Berthet et al., 1998) |

With this is mind, a list of 14 candidate antigens was generated based on their consistent high expression across a variety of growth conditions. These included in vitro chemostat and batch cultures for both *M. tuberculosis* and *M. bovis*, as well as for *M. tuberculosis* infecting macrophages and growing in microaerophillic conditions. In the majority of cases, candidates were also selected based upon a close homology between *M. tuberculosis* and *M. bovis* but with little homology to other mycobacterial species (Table 2). The majority of the candidates are annotated as conserved hypothetical proteins. However, three are putative membrane proteins, one is an excisionase and one a member of the PE family of proteins. Overlapping 20-mer peptides were synthesised for the complete coding sequence of each gene and were grouped into 26 pools of 8 to 12 peptides, with some genes represented by more than one pool. These pools were then screened for their ability to stimulate an IFNγ response in vitro using whole blood from *M. bovis* infected (bovine tuberculin (PPD-B) positive) and 10 *M. bovis* naive (PPD-B negative) cattle.

TABLE 2

Candidate antigens screened

| | | % aa seq homology to *M. tuberculosis* ("*M. tb*") H37Rv if >50% | | | | | | | | | Highly | |
|---|---|---|---|---|---|---|---|---|---|---|---|---|
| Rv | Mb | *M. tb* | *M. bovis* | *M. avium* | *M. paratb* | *M. leprae* | *M. marinum* | *M. smegmatis* | *C. glutamicum* | *N. farcinica* | expressed in†: | Function |
| Rv1211 | Mb1243 | 100 | 100 | | | 94 | 93 | 80 | 52 | 72 | *M. tb** | CHP |
| Rv1222 | Mb1254 | 100 | 100 | 64 | 64 | 71 | 67 | 64 | | | Mb | CHP |
| Rv1398c | Mb1433c | 100 | 100 | | | | | | | | Mtb & Mb | CHP |
| Rv2081c | Mb2107c | 100 | 100 | | | | | | | | Mb | POSSIBLE TP |
| Rv2876 | Mb2901 | 100 | 99 | | | 68 | | 58 | | 50 | Mb | POSSIBLE CONSERVED TP |
| Rv3271c | Mb3299c | 100 | 100 | | | | 78 | | | | Mtb | PROB CONSERVED IMP |
| Rv3407 | Mb3441 | 100 | 100 | | | | | 50 | | | Mtb | CHP |
| Rv3477 | Mb3504 | 100 | 98 | 70 | 70 | 58 | 75 | | | | Mtb & Mb | PE FAMILY PROTEIN (PE31) |
| Rv3613c | Mb3643c | 100 | 100 | | | | | | | | *M. tb** | HP |
| Rv3614c | Mb3644c | 100 | 100 | | | 81 | 73 | 51 | | | Mtb & Mb | CHP |
| Rv3615c | Mb3645c | 100 | 100 | | | 67 | 79 | | | | Mtb & Mb | CHP |
| Rv3633 | Mb3657 | 100 | 100 | | | | | | | | Mb | CHP |

TABLE 2-continued

| Candidate antigens screened | | | | | | | | | | | | |
|---|---|---|---|---|---|---|---|---|---|---|---|---|
| | | % aa seq homology to *M. tuberculosis* ("*M. tb*") H37Rv if >50% | | | | | | | | | Highly | |
| Rv | Mb | *M. tb* | *M. bovis* | *M. avium* | *M. paratb* | *M. leprae* | *M. marinum* | *M. smegmatis* | *C. glutamicum* | *N. farcinica* | expressed in†: | Function |
| Rv3750c | Mb3776c | 100 | 100 | | | | | | | | Mtb | POSSIBLE EXCISIONASE |
| Rv3866 | Mb3896 | 100 | 100 | | | | 89 | 78 | | | Mb | CHP |

†Expressed in all 4 Mtb conditions (batch culture, aerobic and low oxygen chemostats, macrohpages) or 2 Mb conditions (batch and chemostat cultures)

*In all Mtb conditions except low oxygen

CHP: Conserved Hypothetical Protein

HP: Hypothetical Protein

IMP: Integral Membrane Protein

TP: Transmembrane Protein.

All *M. bovis* infected cattle had positive responses to PPD-B and in addition 23 of the 30 infected cattle responded to an ESAT-6/CFP-10 peptide cocktail (Vordermeier et al., 2001). The responder frequencies for all 14 candidate antigens in *M. bovis* infected and *M. bovis* naïve cattle are shown in FIG. 1. Seven of the candidates failed to stimulate any significant IFNγ response in either *M. bovis* infected or naïve cattle. Four of the candidate antigens stimulated a positive response in 10% or more of the *M. bovis* naïve animals. This suggested cross-reactivity with other environmental species even though the inventors had selected against significant homology in mycobacteria other than *M. tuberculosis* or *M. bovis*. Four of the candidates stimulated significant responses in *M. bovis* infected cattle, although two of these were recognised in 10% or less of the cattle tested and had similar or greater responder frequencies in the PPD-B negative animals. Of the two remaining candidates Rv3750c/Mb3776c stimulated a response in 15% of *M. bovis* infected cattle and none of the naïve animals.

Figure 2:
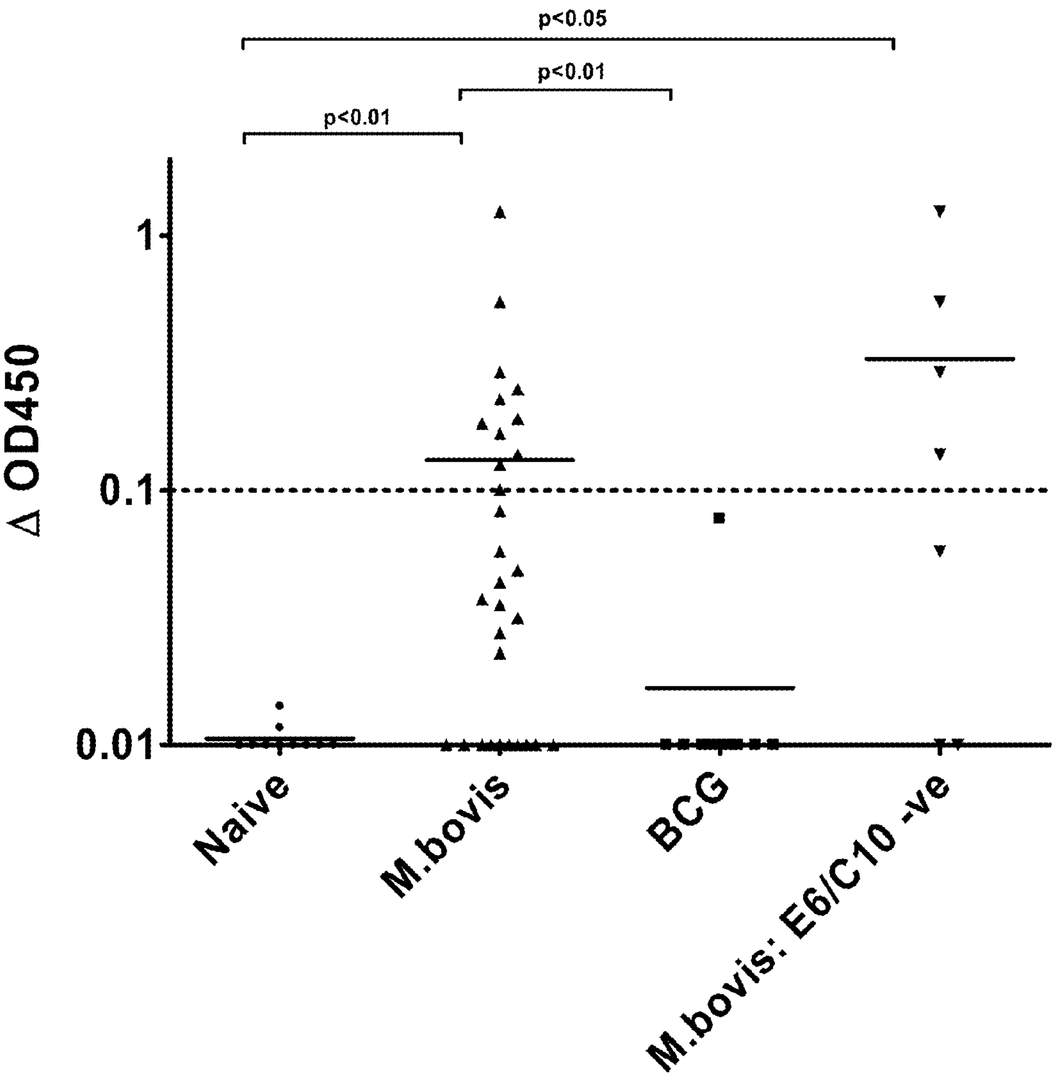
FIG. 2 is a graph showing Mb3645c response in naïve cattle, infected cattle, BCG vaccines and ESAT-6/CFP-10-negative samples. Recitation of E6 and C10 are intended to refer to ESAT-6 and CFP-10, respectively.
Figure 3:
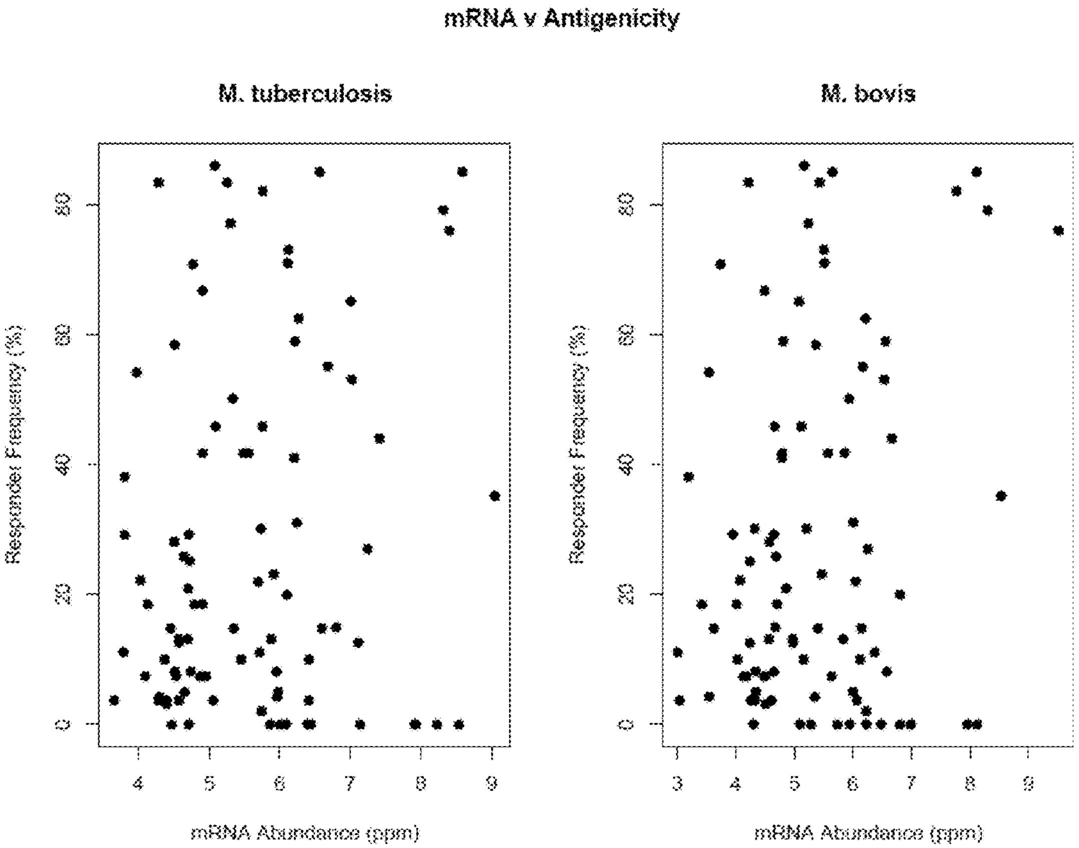
FIG. 3 comprises graphs showing the correlation between mRNA abundance and antigenicity in *M. tuberculosis* (left hand graph) and *M. bovis* (right hand graph)

Mb3645c was not recognised by any of the *M. bovis* naïve cattle, whereas 11 of the 30 *M. bovis* infected animals (37%, p<0.01, FIG. 2) mounted a positive IFNγ response when stimulated with this peptide pool. Interestingly, given the recently proposed role for Rv3615c (the *M. tuberculosis* equivalent to Mb3645c) in the secretion of ESAT-6/CFP-10 in *M. tuberculosis* (Macgurn et al., 2005, Fortune et al., 2005), it was noted that positive responses to the Mb3645c peptide pool from *M. bovis* infected animals were enriched in cattle that did not respond to ESAT-6 or CFP-10 (4 of 7, 57%, p<0.05, FIG. 2). This raises the possibility that these proteins could be used to increase the sensitivity of previously developed ESAT-6/CFP-10 based diagnostic tests (Vordermeier et al., 2001).

To assess Mb3645c's potential as an antigen for differential diagnosis of BCG vaccinated and *M. bovis* infected animals, the peptide pool in 20 BCG vaccinated cattle was screened. In contrast to *M. bovis* infected animals, none of the BCG vaccinated cattle generated a significant IFNγ response to the Mb3645c peptides (p<0.01, FIG. 2).

Finally, as few of the candidates turned out to be potent antigens, the correlation between mRNA levels and antigenicity was further explored. The responder frequencies were collected for an additional 80 mycobacterial proteins that had been screened in *M. bovis* infected cattle (Ewer et al., 2006, Cockle et al., 2002, Mustafa et al., 2006). Together these 94 proteins had responder frequencies that varied from 0 to 86% with an average of 30% so represented a broad range of antigenic potential. In comparison to their mRNA abundances, little correlation was found in either chemostat grown *M. tuberculosis* or *M. bovis:* 0.01 (Spearman's, p=0.38) and 0.06 (Spearman's, p=0.56) respectively, suggesting that mRNA level alone is not a strong predictor for antigenic potential in cattle.

Figure 4:
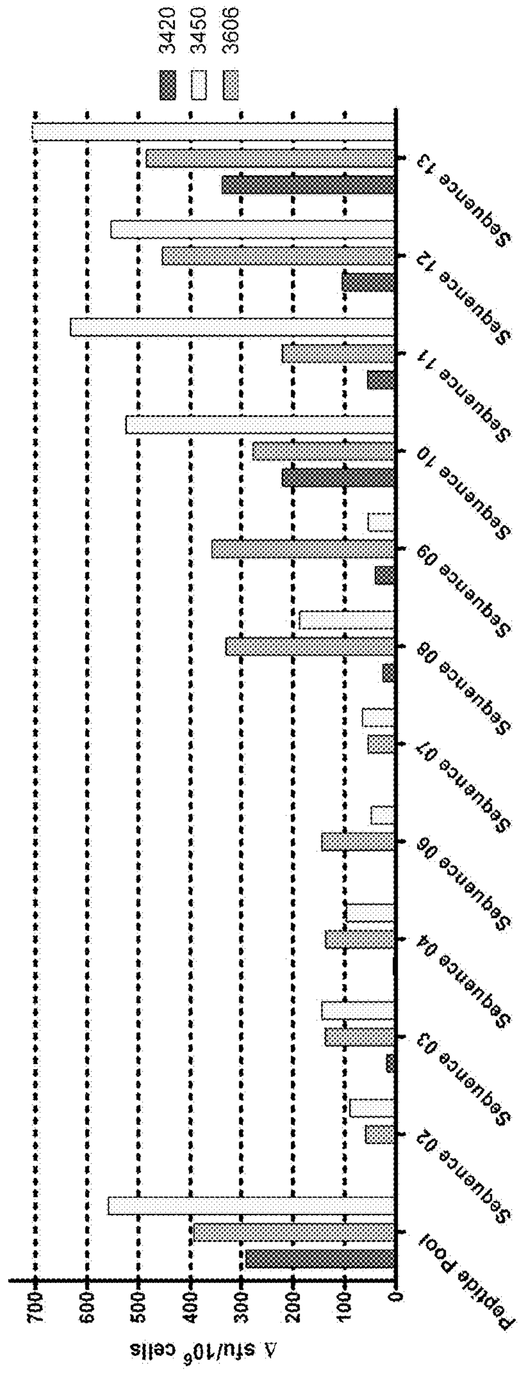
FIG. 4 shows responses of peptides according to the invention, determined using an IFN-γ ELISPOT assay with PBMC isolated from *M. bovis*-infected cattle (sequence 02 corresponds to SEQ ID NO:2, sequence 03 to SEQ ID NO:3 and so on). Numbers 3420, 3450 and 3606 are identifiers for the three cattle tested.

To confirm the presence and location of the T-cell epitopes within Rv3615c, the response to constituent peptides from the Rv3615c pool was determined using an IFN-γ ELISPOT assay with PBMC isolated from *M. bovis*-infected cattle. Peptides SEQ ID NOs: 8-13 were recognized in at least two of the three cattle tested. Peptides SEQ ID NOs: 10-13 (spanning amino acids 57 to 103) from the C terminus of the protein were the most antigenic and were recognized by all three animals tested. Peptide SEQ ID NO:13 (AKIYSEADEAWRKAIDGLFT), in particular, stimulated a response in all three animals, with an average of 509 spot-forming units (SFU) per $10^6$ PBMC (standard deviation, 185.3 SFU per $10^6$ PBMC), which is comparable to the results for the pool as a whole (414 SFU per $10^6$ PBMC; standard deviation, 135.6 SFU per $10^6$ PBMC) (FIG. 4).

Figure 5:
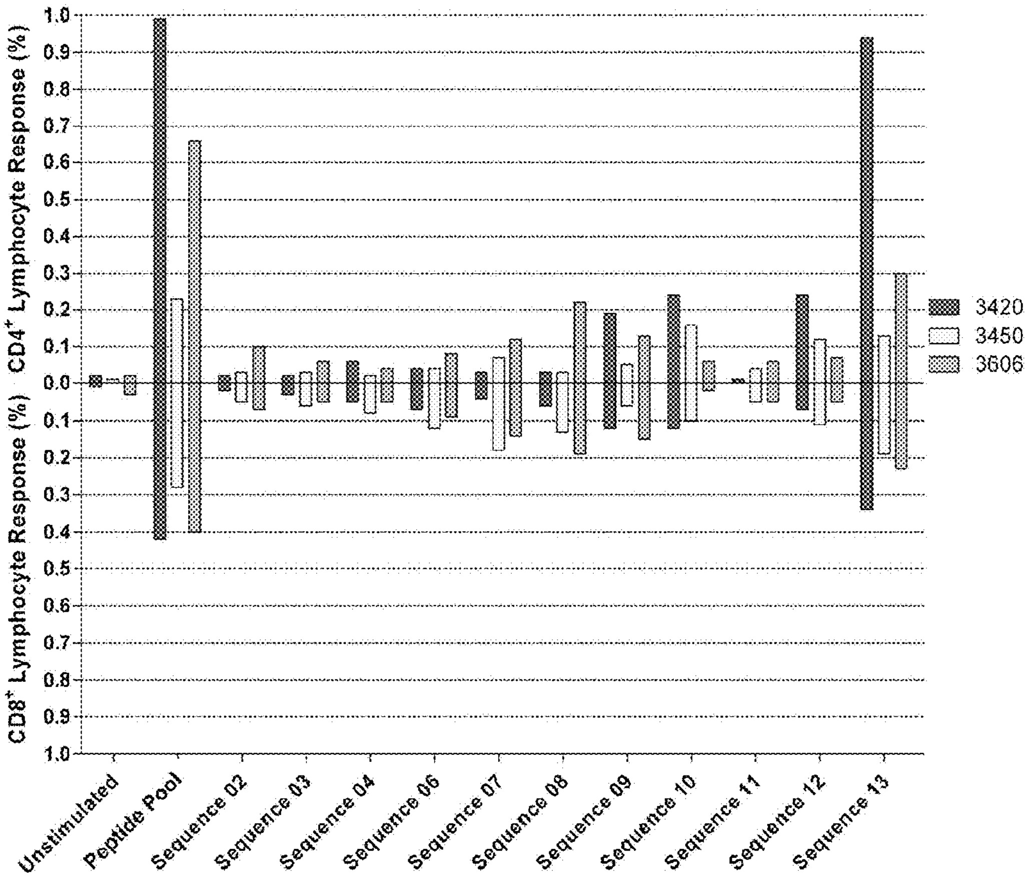
FIG. 5 shows a FACS analysis performed after stimulation of PBMC isolated from *M. bovis*-infected cattle with peptides according to the invention (sequence 02 corresponds to SEQ ID NO:2, sequence 03 to SEQ ID NO:3 and so on, as above). Numbers 3420, 3450 and 3606 are identifiers for the three cattle tested.

To further characterize the specific lymphocyte response to Rv3615c, a FACS analysis was performed with PBMC isolated from the same *M. bovis*-infected cattle that were used for the ELISPOT analysis. Lymphocytes were analyzed for intracellular IFN-γ production and the presence of CD4 and CD8 cell differentiation markers. It was found that, mirroring the ELISPOT data, peptides SEQ ID NO:2-8 stimulated little IFN-γ production. Markedly higher levels of IFN-γ were observed for the cells stimulated with peptides SEQ ID NOs: 9, 10, 12 and 13 (FIG. 5). Interestingly, no IFN-γ response to peptide SEQ ID NO: 11 was observed, despite the fact that a response was recorded in the ELISPOT assay. Analysis of the cells stimulated with peptide SEQ ID NO: 11 showed that the majority (>64%) of the cells in the sample were dead, suggesting that the peptide itself caused IFN-γ-induced apoptosis, which would be in line with the positive responses seen in the ELISPOT assay.

Discussion

There have been many strategies for the identification of mycobacterial immunogens using post-genomic methods including T-cell epitope prediction (Vordermeier et al., 2003) and genomic comparisons to identify pathogen specific open reading frames (Ewer et al., 2006). Previous work had shown that many highly expressed genes were known mycobacterial antigens; therefore, the inventors considered transcriptional activity as a predictor of antigenicity.

A selection of consistently highly expressed genes were screened for their ability to stimulate IFNγ responses from cattle infected with *M. bovis*. Fourteen candidates were selected based on their high expression in both *M. tuberculosis* and *M. bovis* across a variety of growth conditions, including in vitro chemostat and batch cultures, as well as from a macrophage infection and microaerophillic chemostat cultures. Proteins were excluded if they were known immunogens or had significant homology to proteins in other mycobacteria; hence the majority of the candidate antigens had no functional annotation. However, three were predicted membrane associated proteins, one an excisionase and one a PE family protein (Table 2).

Three of the candidates screened here (Rv3615c/14c/13c) appear to be located in the same operon of five genes (Rv3616c to Rv3612c). The entire operon is consistently highly expressed across all of the growth conditions analysed by microarray. One of these candidates—Mb3645c—had the greatest responder frequency in *M. bovis*-infected cattle of all of the candidates tested in this study. The products of these operonic genes have been identified as components of the mycobacterial secretion system (the SNM system), which functions to export both ESAT-6 and CFP-10 (Macgurn et al., 2005, Fortune et al., 2005). The product of the first gene in this operon, Rv3616c, has also been shown to be a dominant mycobacterial antigen. Rv3616c is more frequently recognised in *M. bovis* infected cattle compared to Rv3615c: 84.6% versus 37% (Mustafa et al., 2006). Rv3616c is secreted in a mutually dependent manner with ESAT-6 and CFP-10 (Fortune et al., 2005), whereas Rv3615c appears to interact with other proteins of the secretion system (Macgurn et al., 2005) and may therefore remain within the bacterial cell, which could explain the difference in frequencies of response from *M. bovis* infected cattle.

The ESAT-6/CFP-10 peptide cocktail had been developed as an alternative diagnostic reagent to PPD and differentiates infected and vaccinated individuals as these antigens are not present in *M. bovis* BCG (Vordermeier et al., 2001). The test is reported to have a sensitivity of around 77.9% in infected cattle. Rv3615c has been found not to be recognised by the immune systems of either *M. bovis* naïve or BCG vaccinated animals, unlike Rv3616c to which 40% of vaccinated individuals respond (Mustafa et al., 2006), and is therefore highly specific. Furthermore, 57% of cattle infected with *M. bovis* which do not respond to the ESAT-6/CFP-10 peptide cocktail used did generate a significant IFNγ response to Rv3615c. Therefore, the inclusion of Rv3615c into the ESAT-6/CFP-10 diagnostic cocktail increases the sensitivity of a diagnostic test for *M. bovis*, by detecting infected animals that fail to recognise the ESAT-6/CFP-10 epitopes. This is achieved without compromising test specificity.

Of the initial 14 candidates, just one was significantly antigenic whereas previous observations had led workers to believe that many highly expressed genes could be potent immunogens. It is well known that the processes of transcription and translation are tightly coupled in prokaryotes (Miller et al., 1970) and some correlation between mRNA and protein levels exists in the mycobacteria. It was therefore hypothesised that this was potentially reflecting a trend whereby more abundant proteins are simply more accessible to the host immune systems and more likely to be processed and presented by phagocytes. In light of the data generated by the inventors, this was examined in more detail by collecting responder frequencies for 94 proteins, including the 14 screened in this study. Surprisingly, very little correlation was found between mRNA levels and antigenicity as measured by responder frequencies, suggesting that mRNA abundance alone is not a valid predictor of antigenic status.

REFERENCES

Bacon J, James B W, Wernisch L, Williams A et al. (2004) *Tuberculosis,* 84, 205-217.

Baird, P. N., Hall, L. M. C. and Coates, A. R. M. (1988) *Nucl. Acids Res.,* 16, 9047.

Berthet, F., Rasmussen, P., Rosenkrands, I., Andersen, P. and Gicquel, B. (1998) *Microbiology,* 144, 3195-3203.

Cockle, P. J., Gordon, S. V., Lalvani, A., Buddle, B. M., Hewinson, R. G. and Vordermeier, H. M. (2002) *Infect. Immun.,* 70, 6996-7003.

Colditz, G. A., Brewer, T. F., Berkey, C. S., Wilson, M. E., Burdick, E., Fineberg, H. V. and Mosteller, F. (1994) *JAMA,* 271, 698-702.

Coler, R. N., Skeiky, Y. A. W., Vedvick, T., Bement, T., Ovendale, P., Campos-Neto, A., Alderson, M. R. and Reed, S. G. (1998) *J Immunol,* 161, 2356-2364.

Corbett, E. L., Watt, C. J., Walker, N., Maher, D., Williams, B. G., Raviglione, M. C. and Dye, C. (2003) *Arch Intern Med,* 163, 1009-1021.

DEFRA (2006) *The UK Government Department for Environment, Food and Rural Affairs Bovine TB Expenditure Factsheet* 1999-2005 [online]. Available from: http://www.defra.gov.uk/animalh/tb/stats/expenditure.htm [Accessed 23 Aug. 2006].

Ewer, K., Cockle, P., Gordon, S., Mansoor, H., Govaerts, M., Walravens, K., Marche, S., Hewinson, G. and Vordermeier, M. (2006) *Clin. Vaccine Immunol.,* 13, 90-97.

Fine, P. E. M. (1995) *The Lancet,* 346, 1339-1345.

Fortune, S. M., Jaeger, A., Sarracino, D. A., Chase, M. R., Sassetti, C. M., Sherman, D. R., Bloom, B. R. and Rubin, E. J. (2005) *Proc Natl Acad Sci USA,* 102, 10676-10681.

Harboe, M., Nagai, S., Patarroyo, M. E., Torres, M. L., Ramirez, C. and Cruz, N. (1986) *Infect. Immun.,* 52, 293-302.

Harth, G., Lee, B., Wang, J., Clemens, D. and Horwitz, M. (1996) *Infect. Immun.,* 64, 3038-3047.

Krebs, J. (1997) *Ministry of Agriculture, Fisheries and Food Publications, London, United Kingdom.*

Macgurn, J. A., Raghavan, S., Stanley, S. A. and Cox, J. S. (2005) *Mol Microbiol,* 57, 1653-63.

Miller, 0. L., Jr., Hamkalo, B. A. and Thomas, C. A., Jr. (1970) *Science,* 169, 392-395.

Mustafa, A. S., Skeiky, Y. A., Al-Attiyah, R., Alderson, M. R., Hewinson, R. G. and Vordermeier, H. M. (2006) *Infect. Immun.,* 74, 4566-4572.

R-Development-Core-Team (2006) *R: A Language and Environment for Statistical Computing*, R Foundation for Statistical Computing, Vienna, Austria.

Rogerson, B. J., Jung, Y.-J., LaCourse, R., Ryan, L., Enright, N. and North, R. J. (2006) *Immunology,* 118, 195-201.

Shinnick, T. M. (1987) *J. Bacteria,* 169, 1080-1088.

Skjot, R. L. V., Brock, I., Arend, S. M., Munk, M. E., Theisen, M., Ottenhoff, T. H. M. and Andersen, P. (2002) *Infect. Immun.,* 70, 5446-5453.

Sorensen, A., Nagai, S., Houen, G., Andersen, P. and Andersen, A. (1995) *Infect. Immun.,* 63, 1710-1717.

Vordermeier, H. M., Whelan, A., Cockle, P. J., Farrant, L., Palmer, N. and Hewinson, R. G. (2001) *Clin. Diagn. Lab. Immunol.,* 8, 571-578.

Vordermeier H M, Chambers M A, Cockle P J, Whelan A O, Simmons J, Hewinson R G. (2002). *Infect. Immun.,* 70, 3026-32

Vordermeier, M., Whelan, A. O. and Hewinson, R. G. (2003) *Infect. Immun.,* 71, 1980-1987.

Wood P R, Jones S L. (2001) *Tuberculosis* (Edinb, 81, 147-55.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

All documents cited herein are incorporated by reference in their entirety.

The invention claimed is:

1. A diagnostic reagent for use in the detection of *M. tuberculosis* infection in a mammal, comprising a peptide which has an epitope from a protein having the amino acid sequence of SEQ ID NO: 1, said epitope consisting of consecutive amino acids from within SEQ ID NO: 1, wherein said peptide has fewer than 103 amino acids.

2. The diagnostic reagent according to claim 1, further comprising one or more amino acid sequences each selected from SEQ ID NOS:14-25.

3. A method for diagnosing, in a mammal, infection by or exposure to *M. tuberculosis* versus prior *M. bovis bacillus* Calmette-Guerin (BCG) vaccination, comprising the steps of:

(a) contacting a population of cells from said mammal with a diagnostic reagent according to claim 1;

(b) determining whether cells of said population of cells recognize the diagnostic reagent;

wherein recognition by said population of cells of said diagnostic reagent indicates infection by or exposure to *M. tuberculosis* irrespective of prior *M. bovis bacillus* Calmette-Guerin (BCG) vaccination.

4. The method according to claim 3, wherein determining step (b) comprises comparing IFNγ levels to a control.

5. The diagnostic reagent according to claim 1, wherein said epitope is a T-cell epitope, and wherein said diagnostic reagent is a cell-mediated immunity (CMI) assay diagnostic reagent.

6. The diagnostic reagent according to claim 1, wherein said peptide is a truncated form of SEQ ID NO: 1.

7. The diagnostic reagent according to claim 1, wherein said peptide has up to 20 amino acids, and wherein said epitope has 5 or more amino acids.

8. The diagnostic reagent according to claim 1, wherein said peptide is a synthetic peptide.

9. The diagnostic reagent according to claim 1, wherein said peptide is a recombinant peptide.

10. A fusion protein comprising:

(i) at least one peptide which has an epitope from a protein having the amino acid sequence of SEQ ID NO: 1, said epitope consisting of consecutive amino acids from within SEQ ID NO: 1, wherein said peptide has fewer than 103 amino acids; and (ii) (a) at least one amino acid sequence selected from the group consisting of SEQ ID NOS: 14 and 16-20; or (ii) (b) at least one amino acid sequence selected from the group consisting of SEQ ID NOS: 15 and 21-25.

11. The fusion protein according to claim 10, where said fusion protein comprises at least one amino acid sequence selected from the group consisting of SEQ ID NOS: 16-20 and at least one amino acid sequence selected from the group consisting of SEQ ID NOS: 21-25.

12. A diagnostic kit comprising a diagnostic reagent for use in the detection of *M. tuberculosis* infection in a mammal, comprising:

(a) a peptide which has an epitope from a protein having the amino acid sequence of SEQ ID NO: 1, said epitope consisting of consecutive amino acids from within SEQ ID NO: 1, wherein said peptide has fewer than 103 amino acids; and (b) means for performing a cell-mediated immunity (CMI) assay in a sample from said mammal.

13. The diagnostic kit according to claim 12, further comprising at least one peptide of SEQ ID NOS:16-25.

14. The diagnostic kit according to claim 13, comprising at least one peptide of SEQ ID NOS: 16-20 and at least one peptide of SEQ ID NOS: 21-25.

15. The diagnostic kit according to claim 12, further comprising the amino acid sequences of SEQ ID NOS:14-25.

16. The diagnostic kit according to claim 12, wherein said (b) means for performing a cell-mediated immunity (CMI) assay comprise means for determining IFNγ concentration in said sample.

17. The diagnostic kit according to claim 12, wherein said sample is a blood sample.

18. The diagnostic kit according to claim 12, further comprising at least one peptide of SEQ ID NOS:14-25.

19. A synthetic or recombinant peptide of between 8 to 35 amino acids in length, in which said peptide has an epitope from a protein having the amino acid sequence of SEQ ID NO: 1, said epitope consisting of consecutive amino acids from within SEQ ID NO: 1.

20. The peptide according to claim 19, wherein said peptide is between 10 to 25 amino acids in length.

21. The peptide according to claim 19, wherein said peptide is between 12 to 20 amino acids in length.

22. The peptide according to claim 19, wherein said peptide has *M. tuberculosis*-specific antigenic and/or immunogenic properties.

* * * * *